(12) United States Patent
Lowen et al.

(10) Patent No.: US 7,300,794 B2
(45) Date of Patent: Nov. 27, 2007

(54) ACCELERATED CULTURE SYSTEM FOR INTESTINAL EPITHELIAL CELL MONOLAYERS

(75) Inventors: Marina Lowen, Silver Spring, MD (US); Ali Keshavarz-Shokri, Rockville, MD (US)

(73) Assignee: Supernus Pharmaceuticals, Inc., Rockville, MD (US)

( * ) Notice: Subject to any disclaimer, the term of this patent is extended or adjusted under 35 U.S.C. 154(b) by 435 days.

(21) Appl. No.: 10/797,952

(22) Filed: Mar. 11, 2004

(65) Prior Publication Data

US 2004/0185560 A1    Sep. 23, 2004

Related U.S. Application Data

(60) Provisional application No. 60/455,236, filed on Mar. 17, 2003.

(51) Int. Cl.
*C12N 5/06* (2006.01)
*C12N 5/08* (2006.01)

(52) U.S. Cl. ............. 435/404; 435/405; 435/406; 435/408; 435/371

(58) Field of Classification Search ............. 435/404, 435/405, 406, 408, 371
See application file for complete search history.

(56) References Cited

U.S. PATENT DOCUMENTS 5,712,163 A  *  1/1998  Parenteau et al. .......... 435/405

OTHER PUBLICATIONS

Yamashita et al. "New and better protocols for a short-term Caco-2 cells culture system". Journal of Pharmaceutical Sciences. Mar. 2002. vol. 91, No. 3, pp. 669-679.*
Barka et al. Journal of Histochemistry and Cytochemistry. Nov. 2000. vol. 48, pp. 1453-1460.*

* cited by examiner

*Primary Examiner*—Vera Afremova
(74) *Attorney, Agent, or Firm*—Foley & Lardner LLP

(57) ABSTRACT

The present invention provides a unique medium for the cultivation of intestinal cell lines. The medium allows for the development of a highly differentiated intestinal epithelial cell monolayer in a much shorter period of time than currently possible without the aid of cell culture substrates.

21 Claims, 1 Drawing Sheet

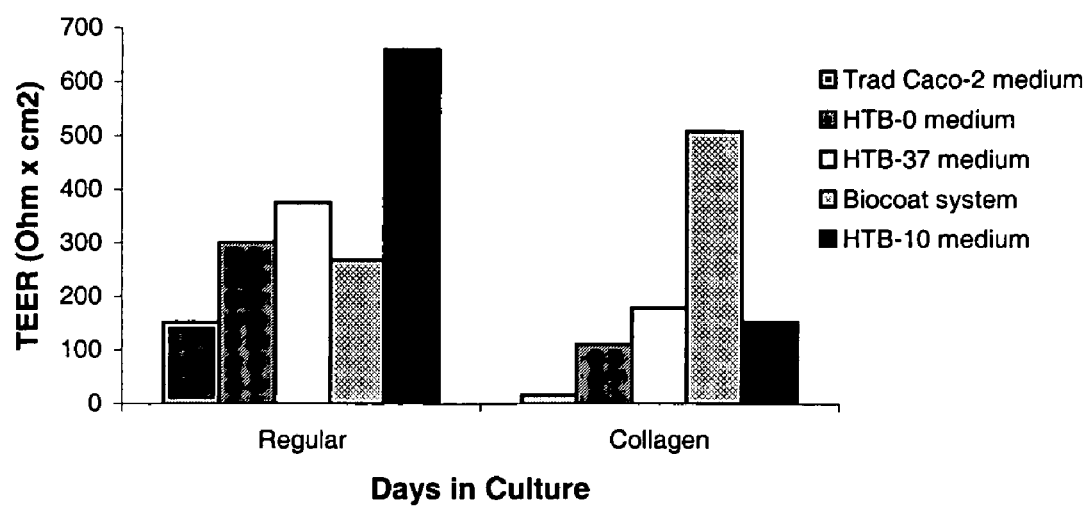

Media:
HTB-10 medium- DMEM/F-12, 10% FBS, hTrf, Hydrocortisone, progesterone, EGF, testosterone, bovine insulin, Na-Butyrate
HTB-0 medium- as above except with 0% FBS
HTB-37 medium- as described in Lentz et al.
Traditional Caco-2 medium- DMEM, 20% FBS
Biocoat System (Collagen)- according to the manufacturer's specification
Biocoat Sytem(Regular)- Biocoat procedures and media used with regular plates

FIGURE 1

ACCELERATED CULTURE SYSTEM FOR INTESTINAL EPITHELIAL CELL MONOLAYERS

This application claims benefit of 60/455,236 filed on Mar 17, 2003.

FIELD OF THE INVENTION

The present invention is directed to a media formulation that allows the development of a highly differentiated intestinal epithelial cell monolayer in a much shorter period of time than currently possible without the aid of cell culture substrates. The invention is also directed to a method of culturing the cells, as well as a process for preparing the specialized media. This is a particular advantage for researchers who rely on such cell lines in studying the intestinal tract, and more particularly for the pharmaceutical industry, which uses these cell lines as models for drug absorption in the intestine.

BACKGROUND OF THE INVENTION

Intestinal epithelium is composed of a monolayer of morphologically polarized cells, which function in absorbing substances from the intestine and transporting them ultimately to the bloodstream. Several epithelial in vitro cell culture systems have been established in the past few decades, which mimic the cells lining the intestine. Some of the cell lines are Caco-2, HT-29, SW 1116, T84, IEC-18, and IEC-6. Caco-2 and HT-29 intestinal cell lines are the most widely used and best characterized systems. Other experimental models that have been under investigation include various clones of these lines (e.g., Caco-2/TC-7 (Caro et al., *Int. J. Pharm.*, 1995, 116), Caco-2BBe (Peterson and Mooseker, *J. Cell Sci.*, 1992 102(3)), HT29-MTX (Pontier et al., *J. Pharm. Sci.*, 2001, 90(10)), co-culturing systems (e.g., Caco-2/HT29-MTX(Walter et al., *J. Pharm. Sci.*, 1996, 85(10)), and primary cell cultures (Fukamachi, *J. Cell Sci.*, 1992, 103).

The cell lines have been an invaluable aid in studies of drug transport, microbial infection, and enzyme induction/regulation. For the most part, Caco-2 cells are the cells of choice for drug transport research and analysis. These cells differentiate spontaneously in culture some time after reaching confluence. Caco-2 cells usually require about 14-30 days after reaching confluence, with an average of 21 days post-confluence, to fully differentiate, i.e. differentiate to the point at which they exhibit many of the morphological, enzymatic, and most importantly, the nutrient transport characteristics of normal human intestinal cells. This is a comparatively long time to wait for cells to be ready to perform experiments, and requires thoughtful long-term planning for conducting studies with this system.

Attempts have been made to decrease the time required for development and differentiation of a Caco-2 cell monolayer, as well as other differentiated epithelial cell cultures. Most of the approaches involve the addition of various differentiation and growth factors to the culture medium, the use of a collagen support for cell attachment, and the reduction of serum requirements in the media. Currently, the 3-day BIOCOAT® HTS Caco-2 assay model (Becton Dickinson Laboratory) is the only commercially available system, and uses fibrillar collagen as cell substrate and serum-free medium. The Biocoat® system allows establishment of a differentiated enterocyte monolayer within three days in a serum-free environment. In this system, the cells are seeded on the Biocoat® Fibrillar Collagen Cell Culture Inserts (Becton Dickinson) and cultured in the specialized medium supplemented with butyric acid, hormones, growth factors and other defined metabolites. The assessment of the Biocoat® and other accelerated systems, such as the one developed by Lentz et al. (Lentz et al., *Pharm. Sci.*, 1998, 1:S456), revealed that these rapid models allow one to determine the rank order of permeability of compounds and give results equivalent to those in the traditional 21-day culture system (Liang et al., *J. Pharm. Sci.*, 2000, 89(3)). However, some of the previously developed accelerated Caco-2 systems have been shown to express low P-glycoprotein (P-gp) levels and have leaky tight junctions. (Liang et al., *J. Pharm. Sci.*, 2000, 89(3)). While the BIOCOAT® system does not exhibit such problems, the use of this commercially available model is quite costly for routine experimental work, because the successful high-throughput culturing of the accelerated Caco-2 system requires frequent purchasing of the specialized media and Fibrillar Collagen Cell Culture Inserts. Moreover, it is unknown whether the collagen coating interferes with drug transport, and thus not provide a true picture of drug absorption, and comparison to the traditional model could be a problem. Therefore, there is a need to develop an inexpensive, non-collagen dependent, rapid Caco-2 model that could be used routinely for high throughput screening of potential drugs.

SUMMARY OF THE INVENTION

An accelerated Caco-2 model has been developed using a novel media formulation that allows development of highly differentiated Caco-2 cell monolayer in about 4 days, as compared to the traditional 21-day culture. The media formulation of the present invention contains certain supplements that, when used together, surprisingly provide an environment conducive to differentiation.

The supplements added to the cell culture medium are fetal bovine serum, nonessential amino acids, transferrin (preferably human), insulin (preferably bovine), epidermal growth factor (preferably human or mouse), sodium butyrate or butyric acid, and the hormones hydrocortisone, progesterone and testosterone.

The present invention is also directed to a process for preparing the medium, as well as a method for using the medium to obtain accelerated growth of an intestinal cell line.

BRIEF DESCRIPTION OF THE DRAWING

FIG. 1 presents the effect of a medium composition on TEER in an accelerated Caco-2 model.

DETAILED DESCRIPTION OF THE INVENTION

An object of the present invention is to provide a composition for culturing intestinal epithelial cell lines, which contains a cell culture growth medium supplemented with fetal bovine serum, nonessential amino acids, human transferrin, bovine insulin, human epithelial growth factor, butyric acid or salts thereof, hydrocortisone, progesterone, and testosterone.

Previous investigations of rapid Caco-2 models revealed that the accelerated differentiation of intestinal epithelial cells is triggered by the synergistic action of nutrients and growth factors contained in a culturing medium. Insulin, epidermal growth factor (EGF), transferrin and various hormones are used routinely as media supplements that facilitate protein and amino acid synthesis, phosphate transport, lipogenesis and cell proliferation. Addition of these and other supplements to cell culture media is especially important when cells are grown in reduced-serum and serum-free conditions. While the exact composition of serum is not defined, it is known to contain a variety of components needed for cell growth and differentiation. For example, insulin provides signals for cell multiplication, while transferrin, EGF and hormones promote cell differentiation (Chopra et al., 1987, *Gastroenterology*, 92; Souleimani and Asselin, 1993, *FEBS Lett.*, 326).

Other co-factors and nutrients that have been mentioned in the literature as supplements for epithelial cell media include cholera toxin (Fukamachi, 1992), selenium, butyric acid and its salts (Gibson et al., 1999; Siavoshian et al., 1997), nucleosides (Sato et al., 2000), and ascorbic acid (Lentz et al., 2000). Most of the previous models were developed in either reduced-serum or serum-free conditions.

While various supplements are known to promote cell growth and/or differentiation, the unique combination of ingredients of the composition of the present invention has not before been described in the literature.

The concentrations of supplements in the media for intestinal epithelial cells can vary somewhat and some amount of optimization for a particular intestinal cell line is to be expected. In general, however, the medium concentrations of insulin, EGF, and transferrin range from 0.01 to 200 µg/mL, while the content of hormones such as progesterone, testosterone, and hydrocortisone should fall between 0.01 and 10 µM. Butyric acid or its salts (such as sodium butyrate), a known differentiation agent, will be effective at concentrations ranging from 0.5 to 5 mM (Siavoshian et al., 1997). For the purposes of drug transport studies, the medium composition is considered optimal when it yields TEER (transepithelial electrical resistance) values of about 200 Ohm×$cm^2$ and above in 4-day-old Caco-2 monolayers that are seeded on regular polycarbonate filters without collagen support (Transwell®, Corning-Costar).

The formulation of the specialized media is based on any of several known cell culture media, and the choice of which one to use should reflect the recommended growth medium for the particular cell line being grown. For instance, the media used for development of the accelerated Caco-2 cell model of the present invention was based on DMEM/F-12 medium supplemented with fetal bovine serum and about 1% nonessential amino acids. Other media could be, for example McCoy's 5a (for HT-29), Eagle's minimal essential medium (for some Caco-2 lines), or RPMI. The media should also contain a source of l-glutamine, typically about 2 to about 4 mM. The concentration of fetal bovine serum is from about 5 to about 20% of the medium formulation.

With respect to transferrin (available, for example from VWR), this can be a human, bovine or mouse form, but preferably is human. As for the epidermal growth factor, either human and mouse can be used interchangeably, although preferred is human.

A preferred specialized accelerated growth medium (named "HTB-10") was prepared for Caco-2 cells by supplementing DMEM/F-12 medium with 10% fetal bovine serum, 1% nonessential amino acids, 100 µg/mL human transferrin, 30 µg/ml bovine insulin, 50 ng/mL human epidermal growth factor (EGF), 2 mM sodium butyrate, and 5 µM of each hydrocortisone, progesterone, and testosterone. The medium optionally, but preferably, contains one or more antibiotics, such as penicillin (at about 100 U/ml), streptomycin (at about 100 µg/ml) and amphotericin B (at about 0.25 µg/ml).

A method of using the medium also is part of the present invention. The following description is representative of how this would be done. Caco-2 cells (available from ATCC, Manassas, Va.) are resuspended in the HTB-10 medium and seeded on 3 µm polycarbonate 6-well Transwell® cell culture inserts (diameter 24.5 mm, Corning Costar) at a density of about $0.2 \times 10^6$ cells/$cm^2$. The seeding of the cells was performed on dry filters by placing 1.5 mL of the cell suspension on the apical side first, followed by addition of 2.5 mL of HTB-10 medium to the baso-lateral side. The cells are grown in a 37° C. incubator at about 95% relative humidity with about 5% $CO_2$.

The experimental comparison of different seeding and culturing approaches revealed that seeding of the cells on dry filters is of crucial importance for obtaining tight monolayers with high TEER values. The reason for this phenomenon is unclear, but may be related to electrostatic properties of polycarbonate surface of the Transwell® filters. To induce cell polarity, the volume of the medium on the apical side was decreased from 1.5 ml to 0.5 mL 48 hours post seeding, and the cells were fed primarily from the baso-lateral side. After the switch, the medium was changed every 24 hr for a total incubation period of 4 days.

The advantages of the invention include: (1) decreased time for obtaining differentiated Caco-2 monolayers for permeability assays; and (2) reduced cost and time of cell culturing and maintenance through the use of ordinary Transwell® plates without collagen support and by reduction of incubation time in culture. The new media of the present invention has allowed for the development of an alternative experimental system with characteristics compatible with traditional 21-day Caco-2 cell model.

EXAMPLES

Example 1

The Use of the specialized accelerated growth medium HTB-10 allowed us to obtain a differentiated Caco-2 monolayer in a 4-day period. The differentiation status and the monolayer integrity were monitored by measurements of transepithelial electrical resistance (TEER) and by determination of permeability of mannitol. Average TEER developed after 4 day culturing in HTB-10 ranged between 420 to 1090 Ohm×$cm^2$. The permeability of mannitol ranged from $0.7 \times 10^{-6}$ to $6.3 \times 10^{-6}$ cm/sec. The accelerated Caco-2 system was also evaluated through a validation process that was based on FDA guidelines for the Biopharmaceuticals Classification System (BCS). In that process, Caco-2 cell permeability coefficients were determined for 26 structurally diverse compounds that were then rank-ordered according to the fraction absorbed in humans. The transport studies were conducted as follows. Drug solutions were prepared in HBSS (pH 7.4) at final concentrations indicated in Table 1. The donor solution of the drug was placed on the apical side of a sample filter (1.5 mL) and the buffer solution (HBSS, pH 7.4) was placed on the baso-lateral side (2.5 mL). The plates were incubated at 37° C. on a shaker for 1-3 hr. Samples were collected at the designated time points and analyzed by either HPLC (uv)or radiometry (for radioactive compounds). The suitability of the accelerated Caco-2 system was validated by determination of permeabilities of several marker compounds including methotrexate, propranolol, and testosterone.

TABLE 1

Permeability of the model compounds used for validation of the accelerated Caco-2 system.

| Drug | Permeability class | Donor concentration, mM | $[P_M \times 10^{-6}]$ cm/sec | % fa in humans* |
|---|---|---|---|---|
| Antipyrine | High | 5.3 | 67.1 +/− 5.5 | 97-100 |
| Caffeine | High | 2.6 | 104.0 +/− 1.0 | 100 |
| Carbamazepine | High | 4.2 | 84.6 +/− 7.2 | 100 |
| Fluvastatin | High | 0.4 | 10.8 +/− 2.2 | 100 |
| Ketoprofen | High | 3.9 | 48.6 +/− 2.8 | 100 |
| Metoprolol | High | 1.5 | 43.6 +/− 8.3 | 95-100 |
| Naproxen | High | 4.3 | 61.2 +/− 8.7 | 94-100 |
| Propranolol | High | 0.0001 | 19.3 +/− 1.9 | 90-100 |
| Testosterone | High | 0.020 | 42.8 +/− 3.3 | 100 |
| Theophylline | High | 5.6 | 46.0 +/− 1.6 | 96 |
| Verapamil | High | 2.0 | 81.9 +/− 10.2 | 100 |
| Atenolol | Medium | 7.5 | 3.1 +/− 0.1 | 50-54 |
| Furosemide | Medium | 3.0 | 1.6 +/− 0.2 | 61 |
| Hydrochlorthiazide | Medium | 3.4 | 6.9 +/− 2.0 | 65-72 |
| Ranitidine | Medium | 2.8 | 2.2 +/− 0.2 | 50-61 |
| Terbutalin | Medium | 0.4 | 5.54 +/− 0.19 | 50-73 |
| Timolol | Medium | 1.2 | 25.4 +/− 0.3 | 72-75 |
| Acyclovir | Low | 14.2 | 3.8 +/− 0.2 | 20-23 |
| Amoxicillin | Low | 5.5 | 0.02 +/− 0.01 | 94** |
| Famotidine | Low | 3.0 | 1.36 +/− 0.27 | 38 |
| Mannitol | Low | 0.014 | 3.0 +/− 0.6 | 16-26 |
| Methotraxate | Low | 0.0007 | 4.2 +/− 0.7 | 20-100** |
| L-alpha-methyldopa | Low | 21.0 | 5.7 +/− 0.5 | 44** |
| PEG-400 | Low | 0.10 | 1.1 +/− 0.1 | N/A |
| PEG-900 | Low | 0.15 | 0.7 +/− 0.1 | 10 |
| PEG-4000 | Low (Zero permeability) | 0.009 | 0.6 +/− 0.1 | 0 |

*reported in the literature
**actively transported compounds

Example 2

The Table 2, below, summarizes the media composition of three comparative systems: Biocoat, Lentz et al., and that of the present invention. Also, FIG. 1 is a graph obtained from the comparison study of the different types of media. Depending on the medium, the seeding was done as described in our procedure (for HTB-10, HTB-0), or according to the Biocoat instructions, or according to the procedure described in Lentz's paper (for HTB-37). The TEERs were measured on the 4th day post-seeding. As can be seen from FIG. 1, the medium of the present invention (in this case, HTB-10) outperformed all of the others in non-collagen supported cell differentiation.

TABLE 2

| Ingredients | HTB-10 | Biocoat ® | Lentz et al. |
|---|---|---|---|
| Cell culturing medium | DMEM/F-12 | DMEM | DMEM/F-12 |
| Fetal Bovine Serum | 10% | − | − |
| Calf Serum (iron supplemented) | − | − | 2% |
| Non-essential amino acids | 1% | − | − |
| Antibiotic/Antimycotic | + | + | − |
| Hydrocortisone | 5 uM | + | − |
| Progesterone | 5 uM | + | − |
| Testosterone | 5 uM | + | − |
| Dexamethasone | − | − | 0.01 uM |
| Estradiol-17B | − | + | − |
| Triiodothyronine | − | + | − |
| EGF (mouse) | 50 ng/mL | + | 50 ng/mL |
| EGF (human) | | | |
| Transferrin (human) | 100 ug/mL | + | 10 ug/mL |
| Insulin (bovine) | 30 ug/mL | + | 10 ug/mL |
| Butyric acid or Sodium Butyrate | 2 mM | + | − |
| Selenium | − | + | − |
| Ascorbic Acid | − | − | 50 ug/mL |
| Bovine pituitary extract | − | − | 50 ug/mL |
| Cholera toxin | − | − | 25 ng/mL |
| Cell seeding density | $0.2 \times 10^6$ cell/cm² | $0.2 \times 10^6$ cell/cm² | $0.2 \times 10^6$ cell/cm² |

TABLE 2-continued

| Ingredients | HTB-10 | Biocoat ® | Lentz et al. |
|---|---|---|---|
| Cell culture inserts | Dry non-collagen Transwell ® filters | Biocoat ® fibrillar collagen filters | Non-collagen Transwell ® filters |

What is claimed is:

1. A composition for culturing intestinal epithelial cell lines, consisting essentially of a cell culture growth medium supplemented with fetal bovine serum, nonessential amino acids, human transferrin, bovine insulin, human epithelial growth factor, sodium butyrate, hydrocortisone, progesterone, and testosterone.

2. The composition of claim 1, wherein the cell growth medium is DMEM/F-12 medium, supplemented with about 1% nonessential amino acids.

3. The composition of claim 1, wherein the concentration of each of human transferrin, bovine insulin and EGF is from about 0.01 to about 200 µg/ml.

4. The composition of claim 1, wherein the concentration of each of hydrocortisone, progesterone, and testosterone is from about 0.01 to about 10 µM.

5. The composition of claim 1, wherein the concentration of sodium butyrate is from about 0.05 to 5 mM.

6. The composition of claim 1, wherein the cell culture medium is supplemented with about 5 to about 20% fetal bovine serum.

7. The composition of claim 2, wherein the concentration of fetal bovine serum is about 10%, the amount of L-glutamine is about 2 µM, the concentration of human transferrin is about 100 µg/mL, the concentration of bovine insulin is about 30 µg/ml, the concentration of human epithelial growth factor is about 50 ng/mL, the amount of sodium butyrate is about 2 mM, and the amount of each of hydrocortisone, progesterone, and testosterone is about 5 µM.

8. A method for culturing an intestinal cell line in vitro, comprising resuspending the cells in a composition consisting essentially of cell culture growth medium supplemented with fetal bovine serum, nonessential amino acids, human transferrin, bovine insulin, human epithelial growth factor, sodium butyrate, hydrocortisone, progesterone, and testosterone; seeding the cells onto dry cell culture inserts; and incubating the cells at 37° C. in 5% Co$_2$.

9. The method of claim 8, wherein the cells are confluent and differentiated in about 4 days.

10. The method of claim 8, wherein the cell growth medium is DMEMIF-12 medium, supplemented with about 1% nonessential amino acids.

11. The method of claim 8, wherein the concentration of each of human transferrin, bovine insulin and EGF is from about 0.01 to about 200 µg/ml.

12. The method of claim 8, wherein the concentration of each of hydrocortisone, progesterone, and testosterone is from about 0.01 to about 10 µM.

13. The method of claim 8, wherein the concentration of sodium butyrate is from about 0.05 to 5 mM.

14. The method of claim 8, wherein the cell culture medium is supplemented with about 5 to about 20% fetal bovine serum.

15. The method of claim 8, wherein the intestinal cell line is a Caco-2 cell line.

16. A process for preparing a composition for culturing intestinal epithelial cell lines consisting essentially of a cell culture growth medium supplemented with fetal bovine serum, nonessential amino acids, human transferrin, bovine insulin, human epithelial growth factor, sodium butyrate, hydrocortisone, progesterone, and testosterone, wherein all ingredients are admixed under sterile conditions.

17. The process of claim 16, wherein the cell growth medium is DMEMIF-12 medium, supplemented with about 1% nonessential amino acids.

18. The process of claim 16, wherein the concentration of each of human transferrin, bovine insulin and EGF is from about 0.01 to about 200 µg/ml.

19. The process of claim 16, wherein the concentration of each of hydrocortisone, progesterone, and testosterone is from about 0.01 to about 10 µM.

20. The process of claim 16, wherein the concentration of sodium butyrate is from about 0.05 to 5 mM.

21. The process of claim 16, wherein the cell culture medium is supplemented with about 5 to about 20% fetal bovine serum.

* * * * *